(12) United States Patent
Daga

(10) Patent No.: US 7,112,191 B2
(45) Date of Patent: Sep. 26, 2006

(54) NEEDLE SAFETY DEVICE FOR AN INTRAVENOUS CATHETER APPARATUS AND METHOD OF USE

(76) Inventor: Neha Daga, Daga House, Kothi Bazar, Betul, Madhya Padesh (IN)

( * ) Notice: Subject to any disclaimer, the term of this patent is extended or adjusted under 35 U.S.C. 154(b) by 255 days.

(21) Appl. No.: 10/868,704

(22) Filed: Jun. 15, 2004

(65) Prior Publication Data

US 2005/0277879 A1 Dec. 15, 2005

(51) Int. Cl.
*A61M 5/00* (2006.01)
(52) U.S. Cl. ............................ 604/263; 604/110
(58) Field of Classification Search ........... 604/110, 604/192, 198, 263, 164.08
See application file for complete search history.

(56) References Cited

U.S. PATENT DOCUMENTS

| | | | |
|---|---|---|---|
| 4,850,977 A * | 7/1989 | Bayless | 604/198 |
| 4,863,434 A * | 9/1989 | Bayless | 604/198 |
| 4,929,241 A * | 5/1990 | Kulli | 604/263 |
| 5,051,109 A * | 9/1991 | Simon | 604/263 |
| 5,053,017 A * | 10/1991 | Chamuel | 604/192 |
| 5,135,504 A | 8/1992 | McLees | |
| 5,558,651 A * | 9/1996 | Crawford et al. | 604/263 |
| 6,117,108 A * | 9/2000 | Woehr et al. | 604/110 |
| 6,585,704 B1 * | 7/2003 | Luther et al. | 604/263 |
| 6,623,458 B1 * | 9/2003 | Woehr et al. | 604/192 |
| 6,652,486 B1 * | 11/2003 | Bialecki et al. | 604/110 |
| 6,916,311 B1 * | 7/2005 | Vojtasek | 604/192 |

* cited by examiner

*Primary Examiner*—Sharon Kennedy
(74) *Attorney, Agent, or Firm*—McKee, Voorhees & Sease, P.L.C.

(57) ABSTRACT

A needle safety device for an intravenous catheter apparatus that includes a base capable of receiving a needle into opposing jaws attached to the base and capable of being influenced by the needle. The jaws move between an expanded position which interact with an obstruction within a wing housing of the intravenous catheter apparatus. The jaws permit relative movement of the needle with the base when expanded, close around a needle tip as it passes the jaws, and prevent relative movement of the needle with the base when the jaws are collapsed. The needle of the intravenous catheter apparatus may then be safely disposed with the needle tip within the needle safety device.

13 Claims, 7 Drawing Sheets

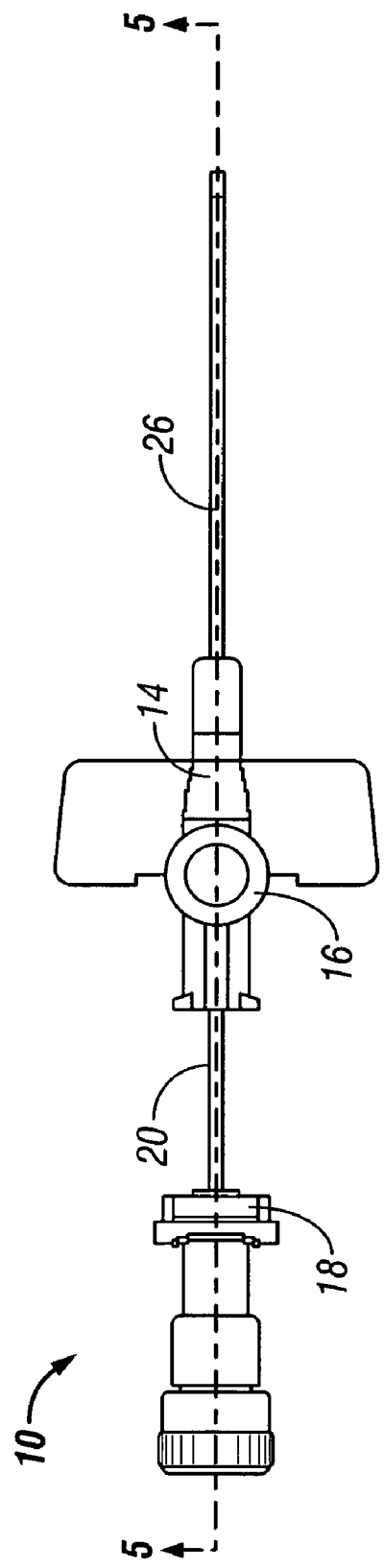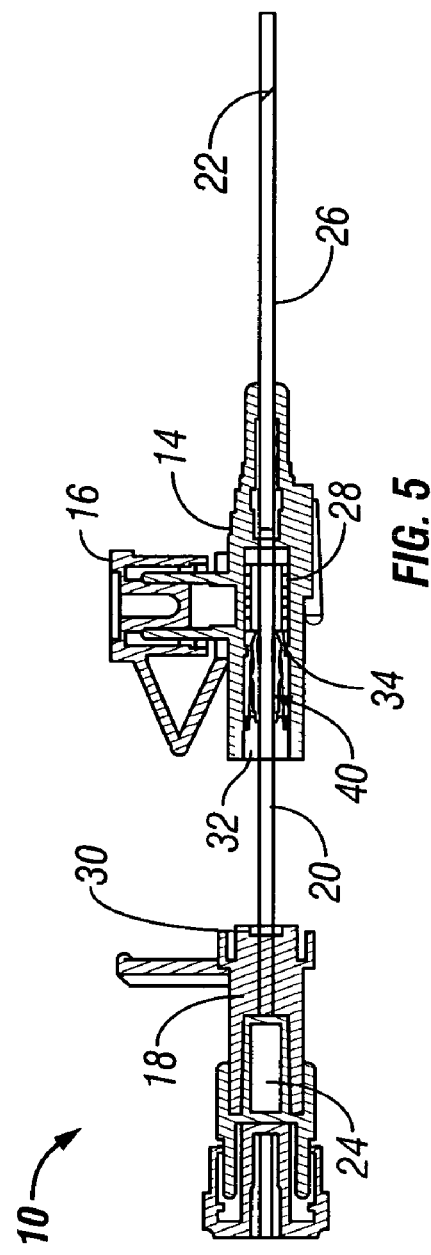

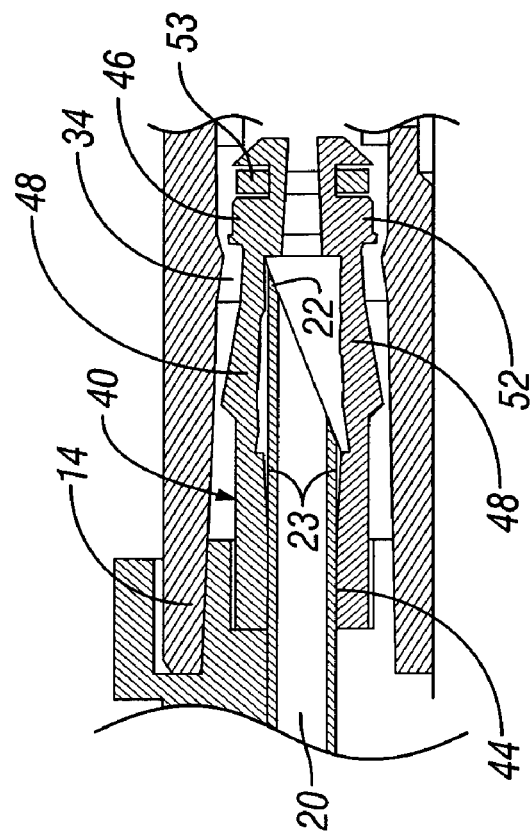
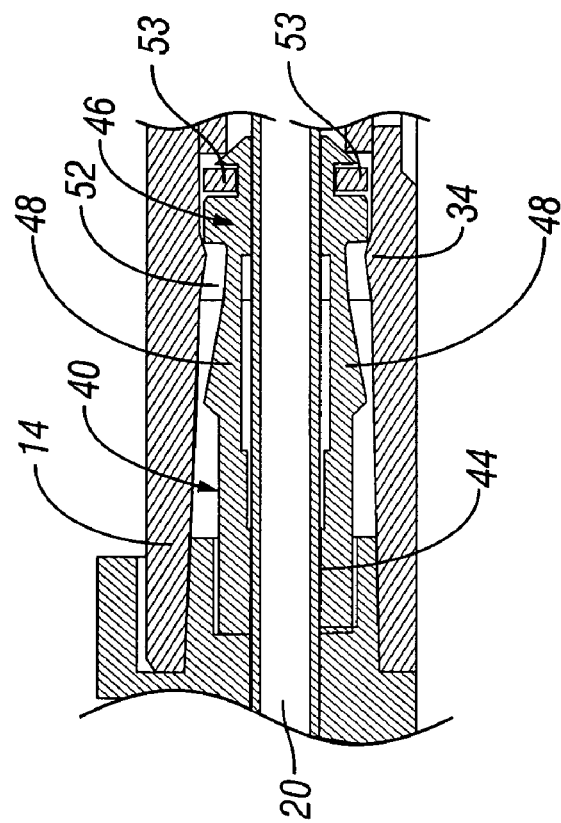

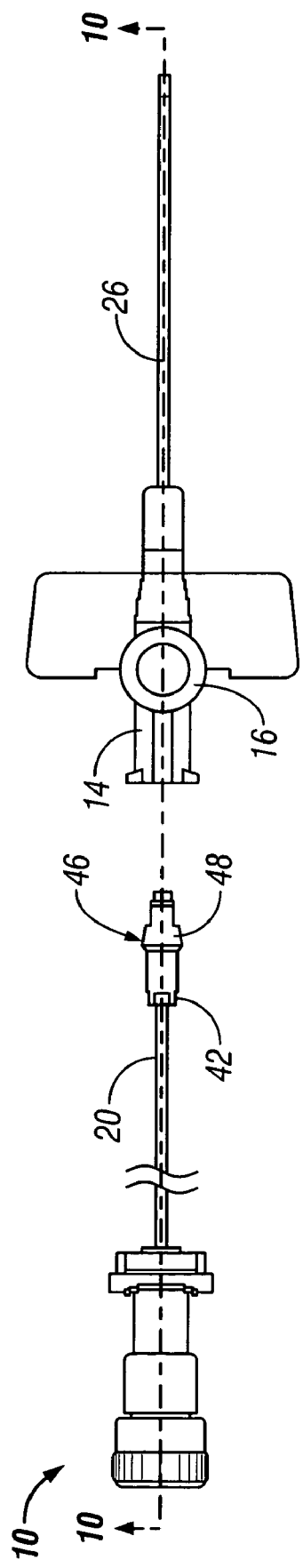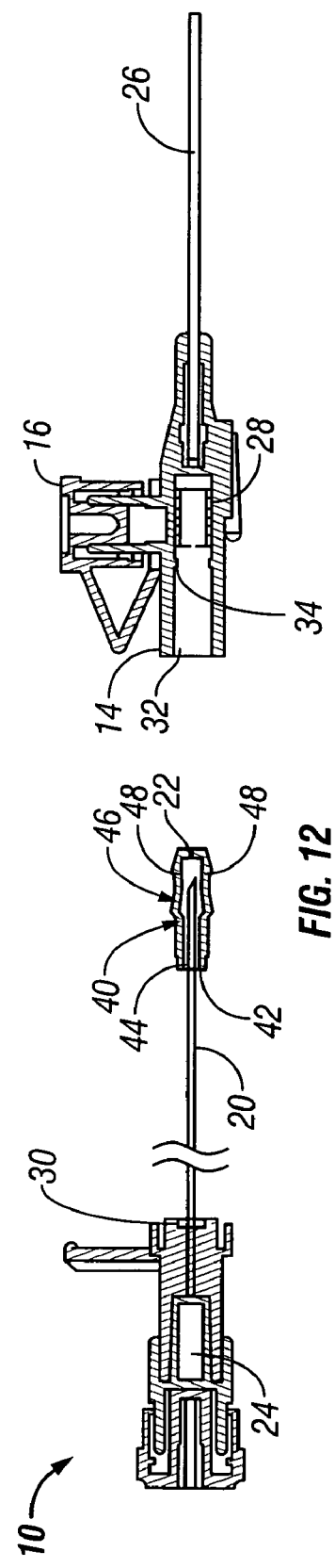
FIG. 11
FIG. 12

NEEDLE SAFETY DEVICE FOR AN INTRAVENOUS CATHETER APPARATUS AND METHOD OF USE

BACKGROUND OF THE INVENTION

The present invention relates to a guard for the needle tip of an intravenous (IV) catheter. In particular, the invention relates to a needle safety device that automatically covers the needle during withdrawal from the patient to prevent accidental contact with medical professionals.

Medical professionals encounter numerous occupational hazards when administering care to patients. One serious hazard is the accidental pricking by a needle after removing from an intravenous catheter. Accidental pricking of medical professionals' skin by the needle is particularly hazardous because the needle tip easily penetrates the latex gloves used by the medical professionals. The concern for accidental pricking is of particular concern in this era of blood borne disease such as Hepatitis or AIDS. Previous needle tip guards have been manufactured that recognize the need for covering the needle tip when being withdrawn from the catheter. The prior art recognizes that the needle tip guard is placed upon the needle after the needle is being withdrawn from the catheter; however, the prior art is difficult to assemble, utilizes an awkward tapered wing housing that requires it to be wider than necessary, utilizes complicated structures and has other disadvantages. These disadvantages will become evident from an examination of U.S. Pat. No. 5,135,504 to McLees and U.S. Pat. No. 6,117,108 to Woehr.

It is therefore a primary objective of the invention to provide a needle safety device in which the disadvantages of the prior art are overcome.

It is a further objective of the present invention to provide a needle safety device in which a cylindrical non-tapered wing housing cylinder is used that reduces the overall size of the intravenous catheter apparatus.

It is a still further objective of the present invention to provide a needle safety device which has a simplified form and is therefore less costly in production and use.

Therefore, the foregoing objectives, other objects, as well as numerous advantages of the present invention, are set forth in the following disclosure.

SUMMARY OF THE INVENTION

The foregoing objectives may be achieved by a needle safety device for an intravenous catheter apparatus having a base capable of receiving a needle and two opposing jaws attached to the base capable of being influenced by the needle. The two opposing jaws together form a reverse collet mechanism. The jaws are moveable between an expanded position with the effective outer diameter of the jaws increased when the needle is between the jaws and a collapsed position when the needle is not between the jaws. The jaws of the needle safety device permit relative movement of the needle with the base when the jaws are expanded. The jaws close around the needle tip as the needle slips through the space between the jaws. The jaws prevent relative movement of the needle with the base when the jaws are collapsed.

The needle safety device may be used with an intravenous catheter apparatus that has a flexible catheter attached to a wing housing. The intravenous catheter apparatus has an inner obstruction within the wing housing. A needle having a needle tip is provided within the flexible catheter in the wing housing. The jaws upon the needle safety device as stated above are moveable between an expandable position wherein the jaws are outwardly moved by the needle and prevented from movement past the inner obstruction in a collapsed position when the jaws close around a needle tip which permits the needle safety device to move past the obstruction while encasing the needle tip.

According to another feature of the present invention, the needle safety device has a ramp portion adapted to permit movement of the needle safety device past an obstruction in the intravenous catheter apparatus when in the expanded position for assembly. The obstruction is most typically an annular ring within the wing housing.

According to another feature of the present invention, the jaws have a side perpendicular to the cylindrical side of the wing housing that prevents movement past an obstruction of the intravenous catheter apparatus while the needle safety device is in an expanded position.

According to another feature of the present invention, the needle safety device is capable of receiving between 14 through 18 gauge needles.

According to another feature of the present invention, the needle safety device is capable of receiving between 18 through 24 gauge needles.

According to another feature of the present invention, the intravenous catheter apparatus has a cylindrical wing housing. The needle safety device fitting efficiently within the cylindrical wing housing.

According to another feature of the present invention, the needle safety device is held in place within a chamber of the needle hub.

According to yet another feature of the present invention, the needle safety device is positioned with the needle safety device abutting a catheter base.

BRIEF DESCRIPTION OF THE DRAWINGS

FIG. 4 is a top view of the intravenous catheter apparatus with the needle partially removed from the catheter and wing housing.

FIG. 5 is a side cross sectional view of FIG. 4 taken along line 5—5.

FIG. 9 is an enlarged cross sectional view of an alternative embodiment of the needle safety device having a flared needle and tension ring with jaws in an open position.

FIG. 10 is the needle safety device of FIG. 9 with jaws in a closed position.

FIG. 11 is a top view of the intravenous catheter apparatus with the needle pulled away from the catheter and wing housing.

FIG. 12 is a side cross-section taken along 9—9 of FIG. 10.

DETAILED DESCRIPTION OF THE PREFERRED EMBODIMENT

Figure 1:
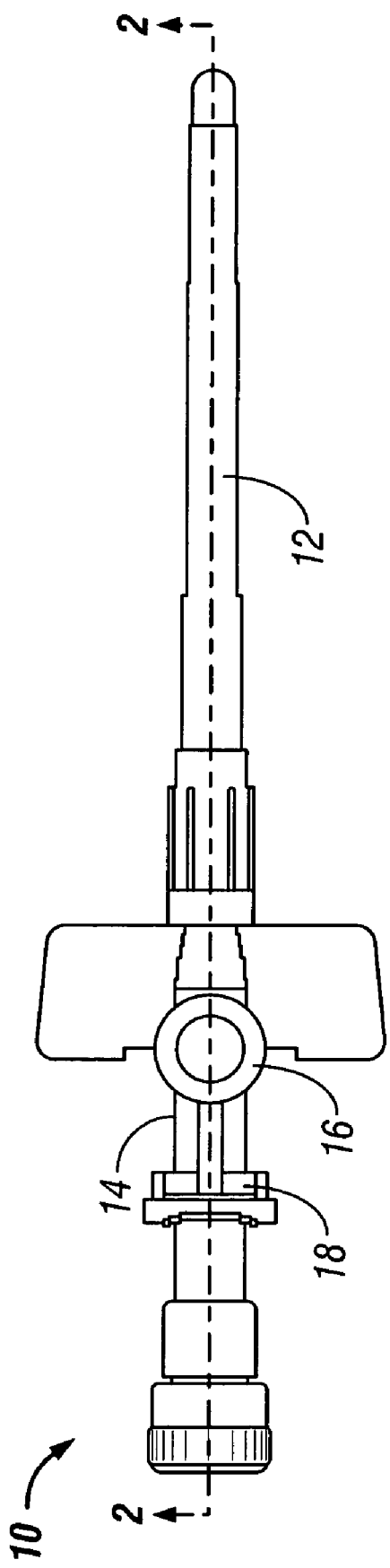
FIG. 1 is a top view of an intravenous catheter apparatus.

Referring to FIG. 1, an intravenous (IV) catheter apparatus 10 of the present invention is shown. The IV catheter apparatus is viewed as a finished product prior to use and includes a needle cover 12, a wing housing 14, a port cap 16 in unitary assembly with the wing housing 14, and a needle hub 18 attached to the wing housing 14.

Figure 2:
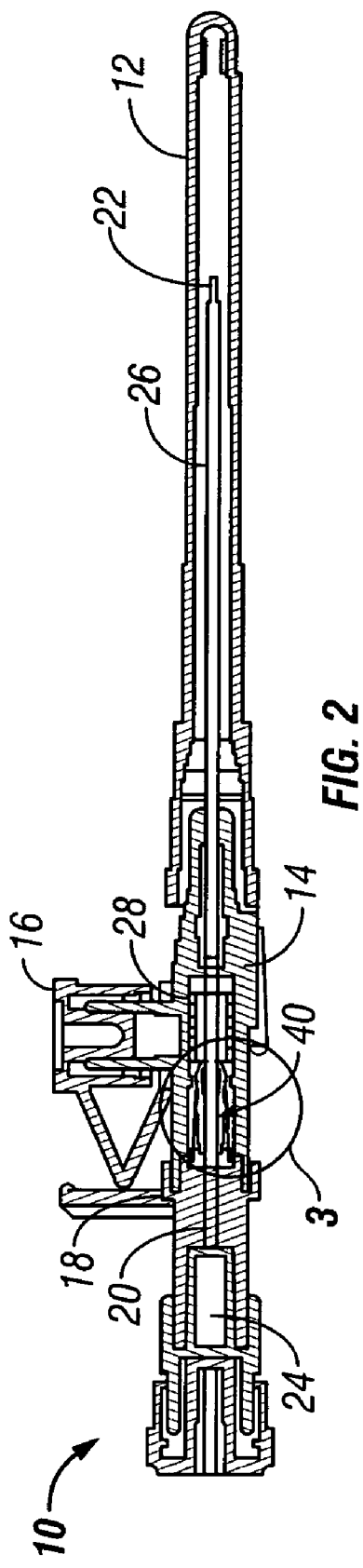
FIG. 2 is a cross sectional view of the apparatus of FIG. 1 taken along line 2—2.

As seen in the cross section depicted in FIG. 2, a needle 20 extends from the needle hub 18 through the wing housing and ends in a needle tip 22 under the needle cover 12.

The needle 20 is hollow and the needle tip 22 is typically cut at a diagonal. When the needle tip 22 is inserted into a patient the needle may encounter fluid pressure which travels through the needle tip 22 through the needle 20 and enters a flash back chamber 24.

Surrounding the needle is a catheter 26 which is attached to the wing housing 14 by catheter base 28. The catheter 26 is a flexible tube that will remain in the user to provide fluids, nourishment, or medicines.

Figure 3A:
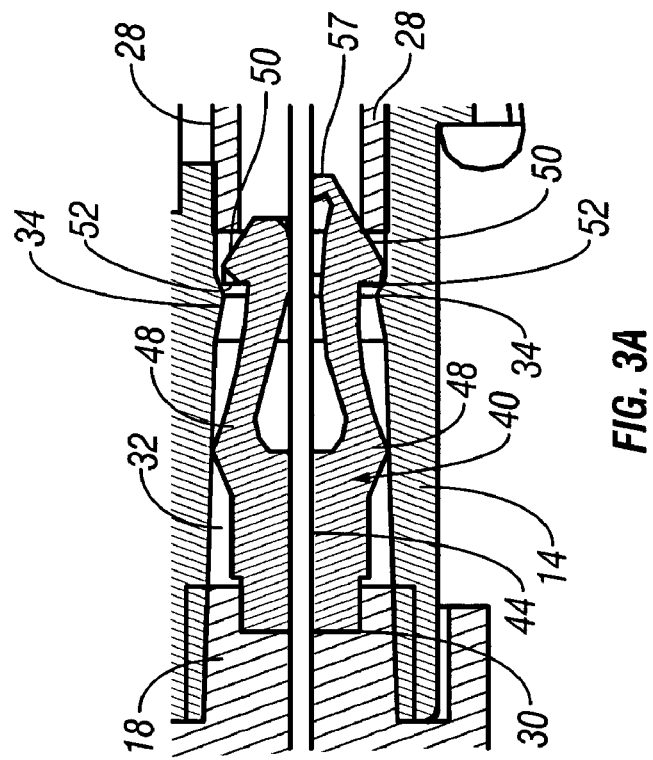
FIG. 3A is an alternative embodiment of the needle safety device of FIG. 3.
Figure 3:
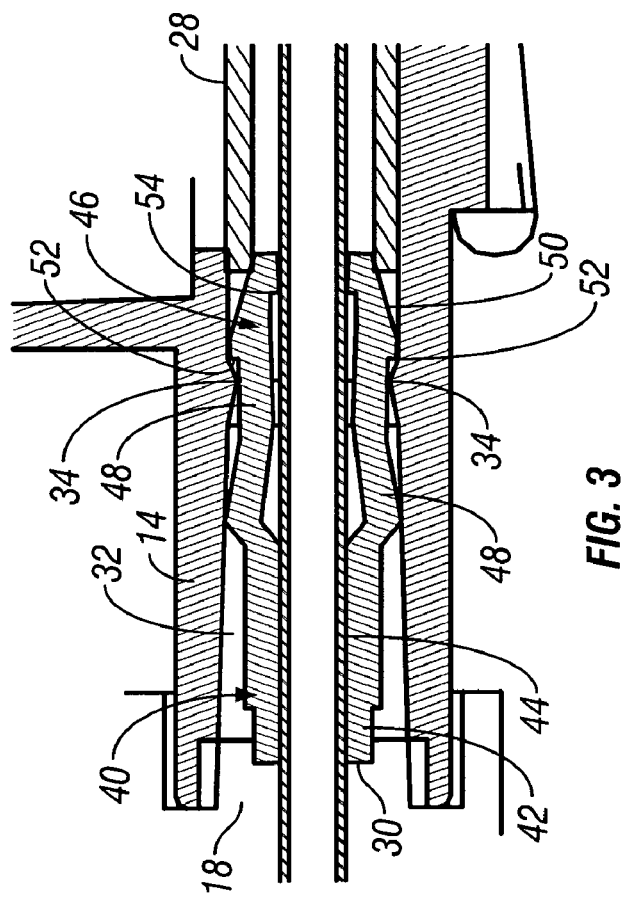
FIG. 3 is an enlarged view of section 3 of FIG. 2.
Figure 6:
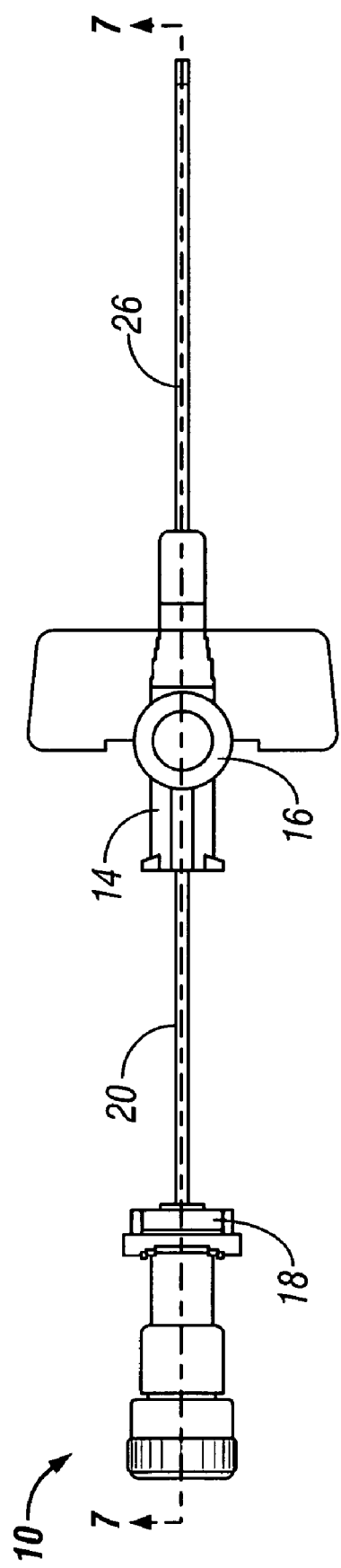
FIG. 6 is a top view of the intravenous catheter apparatus with the needle pulled out of the catheter and the needle out from between the jaws of the needle safety device.
Figure 7:
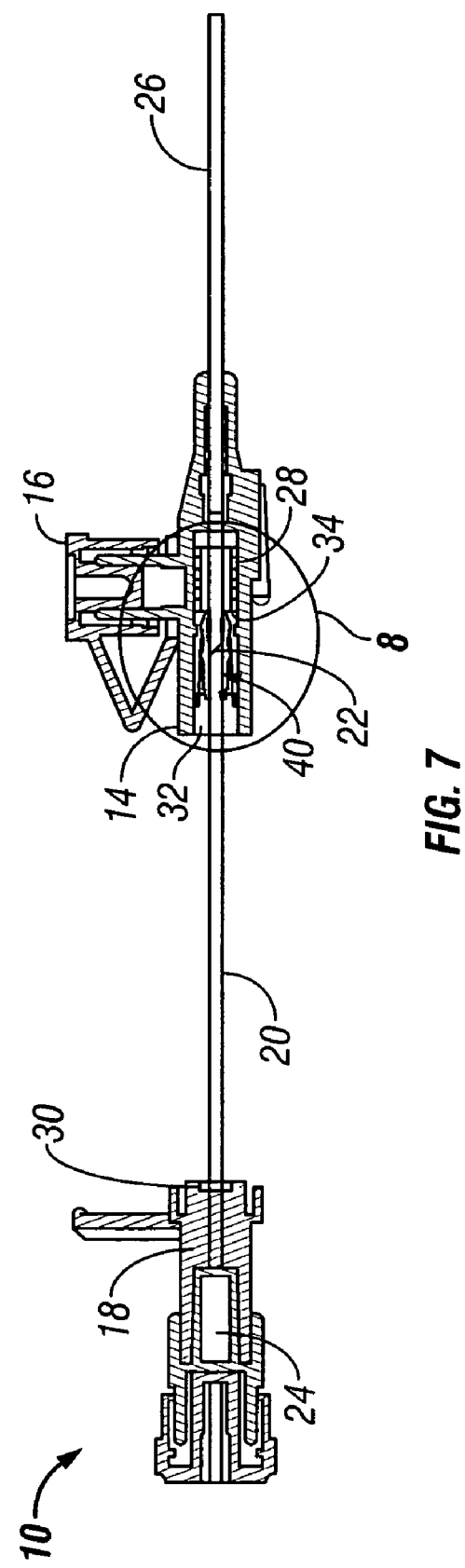
FIG. 7 is a side cross sectional view taken along line 7—7 of FIG. 6.

FIG. 3 is an enlarged view of the needle safety device 40 of FIG. 2. The needle hub 18 has an abutting chamber 30 that is used to hold in position the needle safety device 40 within the wing housing 14. The wing housing 14 has a wing housing chamber 32 in which the needle safety device is placed. Within the wing housing chamber 32 is an obstruction 34 that interacts with the needle safety device 40. In the illustrated embodiment, the obstruction 34 is an annular ring.

The catheter base extends into the wing housing and abuts the needle safety device 40. As illustrated, the needle safety device 40 is held securely in place within the abutting chamber 30 and the catheter base 28.

The needle safety device 40 has a base 42 that has a needle passageway 44 within it. The needle safety device 40 also has a reverse collet 46 that is used to expand to abut the obstruction 34 and to contract to avoid the obstruction 34.

The reverse collet has two jaws 48 moveable between an expanded position with the effective outer diameter of the jaws increased when the needle 20 is between the jaws 48. The jaws move from the expanded position to the collapsed position when the needle 20 is no longer between the jaws 48. The jaws 48 interact with the obstruction 34 to permit relative movement of the needle 20 with the base 42 of the needle safety device 40. The jaws 48 permit this relative motion when they are in the expanded position as seen in the progressive movement between FIGS. 2, 5, 7, and 10.

When the needle 20 passes beyond the jaws 48, the jaws close around the needle tip 22 preventing accidental contact by the medical professional with the needle tip 22. The jaws 48, when closed around the needle tip, prevent relative movement of the needle 20 with the base 42 of the needle safety device 40 because the jaws 48 slip past the obstruction 34 without the obstruction 34 pulling upon the needle safety device 40. The needle safety device 40 is required to be held in place by the obstruction in order for the needle 20 to move relative to the needle safety device 40. The needle passageway 44 of the needle safety device 40 has a frictional co-efficient which grips the needle 20 when the needle safety device 40 is not held in place by the obstruction 34.

As seen in enlarged FIGS. 3, 3A, 8, and 8A, the jaws 48 have a ramp 50. During assembly, the needle safety device 40 is typically placed upon the needle 20 on the end attached to the needle hub 18 and then the end attached into the needle hub 18. The needle safety device 40 is thus expanded prior to being placed within the wing housing 14. As the needle is placed into the catheter the needle safety device 40 is inserted into the wing housing and encounters the obstruction 34. The ramp 50 gradually rides through the obstruction 34 and then fits through the obstruction to provide a positive feel to the assembler. A side 52 opposite the ramp 50 prevents backward movement of the needle safety device 40 once in place past the obstruction 34.

A reverse taper 54 is provided upon the jaws 48. This reverse taper 54 engages the needle tip 22 permitting the needle tip 22 from moving past the reverse taper 54. As seen by comparing FIGS. 3 and 3A, the reverse taper 54 may be on one or both of the jaws 48.

As seen in FIGS. 9 and 10, the needle safety device 40 may utilize a flared needle 23 and a tension ring 53 to keep the needle safety device 40 in protective communication with the needle tip 22. The needle 20 has a flare positioned near its needle point 22 so that its effective diameter increases at that particular point. The flare 23 is created in assembly after the needle safety device 40 is placed onto the needle 20 which is attached to the needle hub 18. The flare 23 ensures that the needle safety device 40 will not be pulled out once the needle tip 22 is trapped in the needle safety device 40. Additionally, a tension ring 53 is provided upon the jaws which will make collapsing of the jaws positive once the needle tip 22 moves past the front of the jaws 48 after the needle 20 is withdrawn out of the catheter 26 after use.

In use, a medical professional receives the intravenous (IV) catheter apparatus with a protective needle cover 12 as seen in FIGS. 1 and 2, the needle 20 and catheter 26 are inserted into a patient's vein. As seen in FIGS. 4 and 5, the needle is then withdrawn from the patient by grasping the wing housing 14 and pulling upon the needle hub 18. The needle 20 slides through the catheter 26 and the needle safety device 40.

Figure 8A:
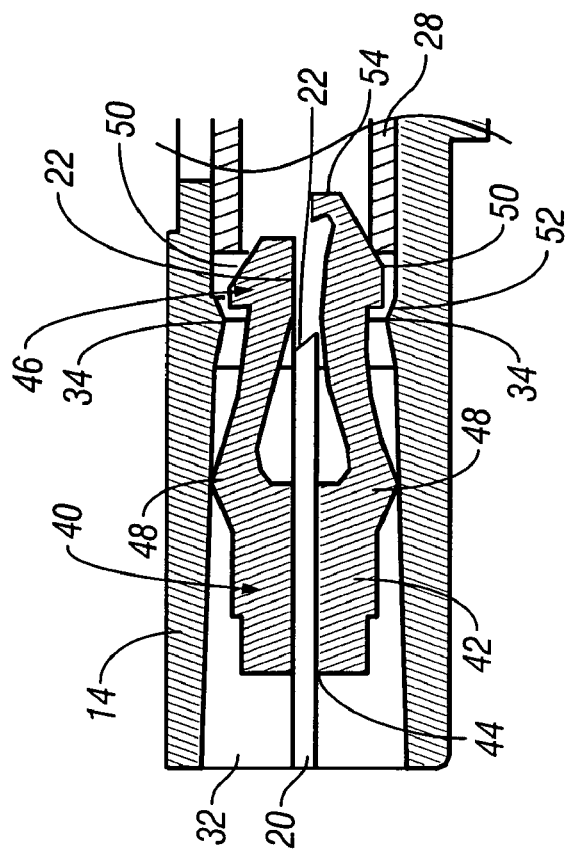
FIG. 8A is an alternative embodiment of the needle safety devices of FIG. 8.
Figure 8:
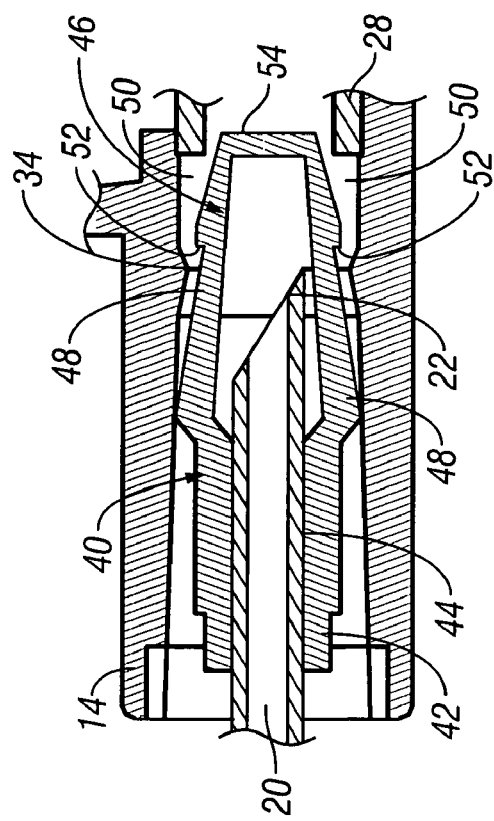
FIG. 8 is an enlarged view of section 8 of FIG. 7.

The needle tip 22 passes the jaws 48 permitting the jaws to collapse to their natural position. Alternatively, the tension ring 53 on the jaws 48 makes collapsing of the jaws 48 positive. In the jaws natural position, they are permitted to pass the obstruction 34 in the wing housing 14. Alternatively, the needle safety device 40 as seen in FIGS. 8 and 8A may still slightly contact the obstruction 34; however, the jaws 48 made of a flexible material and no longer constricted by the metal syringe 22 are permitted to flex slightly to pass the obstruction 34. In this scenario, the needle passageway 44 of the base 42 grips the needle 20 sufficiently for the jaws 48 to pass the obstruction 34. Alternatively, the flare 23 as in FIG. 9 does not pass within the needle passageway 44 permitting the jaws 48 to pass the obstruction 34.

As seen in FIGS. 9 and 10 the medical professional then completely removes the needle safety device 40 past the wing housing 14 for disposal. The device protects the medical professional from accidental pricking by the needle tip 22.

The needle safety device 40 remains in its assembled position as seen in FIG. 1 without affecting the working and functioning of the IV catheter apparatus 10 by having a contoured back portion of the base 42 fit within the needle hub abutting chamber 30. With the base portion 42 in the abutting chamber 30, the jaws are ensured to always be in a plane parallel the needle 20 so that the needle 20 may properly move between the jaws 48 and ensure proper functioning of the needle safety device 40.

The needle tip 22 once within the needle safety device 40 does not come out even if it is pressed against the medical professional, a work surface, or other object. Once the needle safety device 40 is in place, the needle 20 is safe for disposal.

The invention has been shown and described above with the preferred embodiments, and it is understood that many modifications, substitutions, and additions may be made which are within the intended spirit and scope of the invention. In the foregoing, it can be seen that the present invention accomplishes at least all of its stated objectives.

What is claimed is:

1. A needle safety device for an intravenous catheter apparatus, the needle safety device comprising:
   a base capable of receiving a needle;
   two opposing jaws attached to the base capable of being influenced by the needle;
   the jaws moveable between an expanded position with the effective outer diameter of the jaws increased when a needle is through the jaws and a collapsed position when the needle is not through the jaws;
   the jaws permitting relative movement of the needle with the base when expanded, closing around a needle tip, and preventing relative movement of the needle with the base when collapsed;
   the jaws having a tension ring positively collapsing the jaws.

2. The needle safety device of claim 1 wherein the jaws have a ramp portion adapted to permit movement past an obstruction of the intravenous catheter apparatus when in the expanded position for assembly.

3. The needle safety device of claim 1 wherein the jaws have a side adapted to prevent movement past an obstruction of the intravenous catheter apparatus when in the expanded position.

4. The needle safety device of claim 1 wherein the base receives between 14 to 18 gauge needles.

5. The needle safety device of claim 1 wherein the base receives between 18 to 24 gauge needles.

6. The needle safety device of claim 1 wherein the jaws have a reverse taper adapted to create a barrier against movement of a needle tip once the jaws are moved to the collapsed position.

7. A needle safety device for an intravenous catheter apparatus, the needle safety device comprising:
   a housing having a housing chamber therein, the housing having an obstruction extending into the housing chamber;
   a base having an exterior surface and including two or more flexible jaws extending from the base and a needle passageway extending through the base;
   at least one of the flexible jaws having a side on the exterior surface of the base;
   the flexible jaws having ends that are biased to a collapsed position engaging one another to enclose the passageway, the jaws having sufficient flexibility to move to an expanded position wherein the ends of the jaws are separated from one another;
   a needle having a tip extending through the needle passageway and outwardly beyond the ends of the jaws and urging the ends of the jaws to the expanded position;
   the needle being movable to cause the tip thereof to be within the passageway of the flexible base whereby the flexibility of the flexible jaws causes the ends of the jaws to move to their collapsed position enclosing and protecting the tip of the needle;
   the side on the exterior surface of the one of the flexible jaws engaging the obstruction of the housing to prevent removal of the base and flexible jaws from the chamber of the housing when the ends of the jaws are in the expanded position and being free to clear the obstruction when the ends of the jaws are in the collapsed position so as to permit removal of the jaws from the housing chamber;
   the tip of the needle being flared to engage the passageway and prevent removal of the tip of the needle from the passageway of the base when the ends of the jaws are in the collapsed position.

8. The intravenous catheter apparatus of claim 7 wherein the jaws have a ramp portion permitting movement of the needle safety device past the obstruction during assembly.

9. The intravenous catheter apparatus of claim 7 wherein at least one jaw has a reverse taper to create a barrier to prevent accidental movement of the needle tip out of the needle safety device.

10. The intravenous catheter apparatus of claim 7 further comprising a needle hub attached to the needle, an abutting chamber within the hub, the needle safety device based fitting within the abutting chamber to align the needle safety device with the needle.

11. The intravenous catheter apparatus of claim 7 wherein the obstruction is an annular ring.

12. A method of using an intravenous catheter apparatus having an inner obstruction within a cavity of a wing housing and a needle safety device that interacts with the inner obstruction, the method comprising:
   placing the needle safety device within the cavity of the wing housing, the needle safety device having a base and two or more jaws extending from the base, the jaws having jaw ends; at least one of the jaws having a side projecting from an outer surface thereof, a passageway extending through the needle safety device;
   surrounding the jaws with a tension ring so as to bias the jaws toward a collapsed position wherein the ends of the jaws engage one another and the side is free from engaging the obstruction and from preventing removal of the needle safety device from the cavity of the wing housing;
   inserting a needle having a needle tip thereon in a first direction through a passageway in the needle safety device and into a patient, whereby the needle engages the ends of the jaws and moves the jaws to an expanded position wherein the side engages the obstruction and prevents the removal of the needle safety device from the cavity of the wing housing;
   withdrawing the needle from the patient;
   moving the needle through the passageway in a second direction opposite from the first direction until the needle tip is completely within the passageway and the jaws are permitted to return to the collapsed position protecting and enclosing the needle tip within the passageway;
   removing the needle safety device from the cavity of the wing housing with the needle tip enclosed within the passageway and protected by the ends of the jaws.

13. The method of claim 12 comprising using an annular ring for the obstruction.

* * * * *